US010733561B2

United States Patent
Sullivan et al.

(10) Patent No.: US 10,733,561 B2
(45) Date of Patent: Aug. 4, 2020

(54) SYSTEM AND METHOD FOR ANALYZING MEDIA FOR TALENT DISCOVERY

(71) Applicants: Dion Sullivan, Mill Valley, CA (US); Joshua Heenan, Oakland, CA (US); Roman Akulshin, Walnut Creek, CA (US); Eric Crook, San Francisco, CA (US)

(72) Inventors: Dion Sullivan, Mill Valley, CA (US); Joshua Heenan, Oakland, CA (US); Roman Akulshin, Walnut Creek, CA (US); Eric Crook, San Francisco, CA (US)

(*) Notice: Subject to any disclaimer, the term of this patent is extended or adjusted under 35 U.S.C. 154(b) by 265 days.

(21) Appl. No.: 15/877,118

(22) Filed: Jan. 22, 2018

(65) Prior Publication Data
US 2018/0189709 A1    Jul. 5, 2018

Related U.S. Application Data

(60) Provisional application No. 62/442,423, filed on Jan. 4, 2017.

(51) Int. Cl.
*G06Q 10/06* (2012.01)
*G07C 13/00* (2006.01)
(Continued)

(52) U.S. Cl.
CPC ..... *G06Q 10/06398* (2013.01); *A61K 9/0014* (2013.01); *A61K 9/06* (2013.01); *A61K 31/375* (2013.01); *A61K 36/23* (2013.01); *A61K 36/886* (2013.01); *A61K 38/1825* (2013.01); *A61K 38/1841* (2013.01); *A61K 38/2066* (2013.01); *A61K 47/10* (2013.01); *A61K 47/32* (2013.01);
(Continued)

(58) Field of Classification Search
CPC ............. H04N 21/466; H04N 21/4668; H04N 21/23418; G06N 20/00; G06N 3/02; G06K 9/00369
See application file for complete search history.

(56) References Cited

U.S. PATENT DOCUMENTS

| 7,227,893 B1 | 6/2007 | Srinivasa et al. |
| 7,650,319 B2 * | 1/2010 | Hoffberg ............ G05B 19/0426 706/45 |

(Continued)

*Primary Examiner* — Yosef Kassa
(74) *Attorney, Agent, or Firm* — Eandi Fitzpatrick LLP (57) ABSTRACT

A method for analyzing media to evaluate talent of a subject portrayed in the media is provided. The steps describe receiving a plurality of the media at a server, the media being performance based media; transforming the media into at least a data set corresponding to at least a characteristic of the media at the server, wherein the server is in communication with a node; identifying features in the data set that correspond to a probability of success of the subject in the media; receiving subjective opinion polling data from a plurality of participants as to whether the subject in the media has talent; training the node via machine learning algorithm to identify, using the identified features in the data set and the subjective opinion polling data provided, whether the subject is likely to have talent; and executing the machine learning algorithm to output a score relating to the talent of the subject in the media. A system for discovering talent is also provided herein.

18 Claims, 8 Drawing Sheets

(51) Int. Cl.

| | | |
|---|---|---|
| *G06Q 10/10* | (2012.01) | |
| *G06K 9/00* | (2006.01) | |
| *G06K 9/62* | (2006.01) | |
| *G06K 9/66* | (2006.01) | |
| *G06N 20/00* | (2019.01) | |
| *A61K 9/06* | (2006.01) | |
| *A61K 47/32* | (2006.01) | |
| *A61P 17/10* | (2006.01) | |
| *A61P 17/00* | (2006.01) | |
| *A61P 17/02* | (2006.01) | |
| *A61K 9/00* | (2006.01) | |
| *A61K 31/375* | (2006.01) | |
| *A61K 36/23* | (2006.01) | |
| *A61K 36/886* | (2006.01) | |
| *A61K 38/18* | (2006.01) | |
| *A61K 38/20* | (2006.01) | |
| *A61K 47/10* | (2017.01) | |
| *A61K 47/34* | (2017.01) | |
| *A61K 47/36* | (2006.01) | |
| *G06Q 50/00* | (2012.01) | |

(52) U.S. Cl.
CPC .............. *A61K 47/34* (2013.01); *A61K 47/36* (2013.01); *A61P 17/00* (2018.01); *A61P 17/02* (2018.01); *A61P 17/10* (2018.01); *G06K 9/00369* (2013.01); *G06K 9/6202* (2013.01); *G06K 9/6268* (2013.01); *G06K 9/66* (2013.01); *G06N 20/00* (2019.01); *G06Q 10/1053* (2013.01); *G07C 13/00* (2013.01); *G06Q 50/01* (2013.01)

(56) References Cited

U.S. PATENT DOCUMENTS

| | | | |
|---|---|---|---|
| 7,966,078 B2 * | 6/2011 | Hoffberg | G05B 15/02 |
| | | | 700/17 |
| 7,973,584 B2 * | 7/2011 | Washizu | G01R 31/2841 |
| | | | 327/164 |
| 8,516,266 B2 * | 8/2013 | Hoffberg | G05B 15/02 |
| | | | 713/151 |
| 8,649,613 B1 * | 2/2014 | Leung | G06K 9/00724 |
| | | | 382/155 |
| 9,317,908 B2 | 4/2016 | Seow et al. | |
| 9,349,054 B1 | 5/2016 | Saitwal et al. | |
| 9,454,884 B1 | 9/2016 | Chen et al. | |
| 9,460,522 B2 | 10/2016 | Saitwal et al. | |
| 9,471,844 B2 | 10/2016 | Saitwal et al. | |
| 9,473,758 B1 | 10/2016 | Long | |
| 9,483,707 B2 | 11/2016 | Chen | |
| 2009/0281981 A1 | 11/2009 | Chen et al. | |
| 2010/0312769 A1 | 12/2010 | Bailey et al. | |
| 2011/0188715 A1 | 8/2011 | Shotton et al. | |
| 2012/0106800 A1 | 5/2012 | Khan et al. | |
| 2012/0185544 A1 | 7/2012 | Chang et al. | |
| 2012/0197651 A1 * | 8/2012 | Robinson | G06Q 30/02 |
| | | | 705/1.1 |
| 2012/0207359 A1 | 8/2012 | Konukoglu et al. | |
| 2013/0260357 A1 * | 10/2013 | Reinerman-Jones | |
| | | | G06Q 10/1053 |
| | | | 434/362 |
| 2016/0171852 A1 | 6/2016 | Lin et al. | |
| 2016/0173882 A1 | 6/2016 | Mishra et al. | |
| 2016/0180192 A1 | 6/2016 | Ayvaci et al. | |
| 2016/0247119 A1 * | 8/2016 | Goates | G06Q 10/1053 |
| 2017/0161366 A1 * | 6/2017 | Maitra | G06F 16/3344 |

\* cited by examiner

SYSTEM AND METHOD FOR ANALYZING MEDIA FOR TALENT DISCOVERY

CROSS-REFERENCE TO RELATED APPLICATIONS

This application claims the benefit of U.S. Provisional Application No. 62/529,929 entitled System and Method for Analyzing and Tracking Media for Talent Discovery, filed on Jul. 7, 2017.

FIELD OF THE INVENTION

The present invention relates generally to system and methods used for media recognition, tracking and analysis. More particularly, the present invention relates to certain new and useful advances in computer-based systems utilizing machine learning methodologies that can be used by companies to automate the discovery of quality media (e.g., images, videos, writings) and talent (e.g., musicians, singers, dancers, athletes, comedians, artists, film makers, actors, etc.) across a variety of creative platforms (e.g., YouTube, Instagram, Twitter) based upon the analysis of media in which in any of the talent appears in; reference being had to the drawings accompanying and forming a part of the same.

BACKGROUND OF THE INVENTION

The basic idea of identifying talent is commonplace across many industries, but it becomes especially important in the entertainment industry where agents, managers, producers, directors and other creatives are attempting to find the next great talent to represent or work with.

In talent management, two key areas of focus are (1) performance and (2) potential. Understanding an individual's potential, meaning one's future performance, is an integral aspect of talent management. These foci run across various industries and talent spaces, as for example, actors, authors, directors, models, musicians, producers, writers and the like.

Many talent agents work for a talent agency, which arms them with many departments and recourses to analyze any potential talent in their quest for finding the next greatest thing. Before the digital age, many talent agents spent hours in bars, casting halls, studio halls and wherever else they had a lead about places to find the next greatest talent. Often, these leads would be useless and the agents would be left with nothing to show for all their effort. Other times, the agent may catch a break and find someone worth representing—in other words, a lot of talent scouting may be pure luck. For example, Jennifer Lawrence, the star of some of the biggest grossing box offices such as the Hunger Games, Joy, American Hustle and Silver Lining Playbook, was discovered randomly while on a family vacation at the age of 14 by a talent agent who just happened to see her and thought she would be great for TV.

However, as technology has evolved, the ways through which talent may be found have expanded—most notably, the advent of social media has taken talent discover away from the days of hopping from bar-to-bar performances, to browsing digital performances found at your fingertips without ever having to leave the comforts of your office or home.

Social media is the use of web-based technologies, computers and mobile technology (e.g., smartphones) to create highly interactive platforms through which individuals, communities and companies can share, create, discuss and modify user-generated content or pre-made content already posted online. Social media differs from traditional forms of media such as paper and TV broadcasting in many ways, including larger reach, frequency, usability, immediacy and permanence. Social media involves a large number of users that interact socially with one another and freely express and share opinions among themselves.

It can be argued that social media truly came to age in the early 2000s, with the advent of social networking sites MySpace® and Facebook®. Currently, the most popular social media websites are the content communities such as Instagram, Facebook®, Snapchat® and most notably, YouTube®—interesting enough, theses content communities, where individuals create accounts to share their creative works and thousands flock to see their work, have led to the discovery of many previously undiscovered talent One of the most famous example of talent discovery from these digital content communities is singer Justin Bieber, who was discovered in 2007 on the then-new video sharing platform, YouTube. When Atlanta based promoter Scooter Braun was searching the site for someone, he stumbled across a video of then 12-year-old Justin Bieber singing a song by Chris Brown. Fast forward ten years and Justin Bieber has won over 144 awards and was named as one of Forbes' most influential celebrities; at the same time, and Scooter Braun has gone on to become a successful manager who continues to use technology to his advantage when scouting and locating talent, even discovering more talent in YouTube®. Ever since the discovery of Justin Bieber on YouTube®, others have followed similar paths to attempt to discovery the next greatest talent, and have had success.

Other famous musicians who have been discovered on YouTube include Carly Rae Jepsen, Shawn Mendes, Alessia Cara, Charlie Puth, The Weeknd, Austin Mahone, Pentatonix and Ed Sheeran. Even though YouTube® is credited as being where these individuals were "discovered," they were all on multiple social media platforms (e.g., Vine®, Facebook®, Twitter®) and appeared in other media outlets (e.g., American Idol®), where anyone could have discovered them. However, without any metrics or specific method for which users track and rank these individuals based on their content put forth on those platforms and media outlets, these individuals went undiscovered until someone noticed them on YouTube® as a result of going "viral."

Advances in technology not only allow creatives to share their talents, but can also help individuals and companies better locate such talent.

For example, data mining is a technique by which hidden patterns may be found in a group of data. Typically implemented as software or in association with database systems, data mining does not just change the presentation of data but actually discovers previously unknown relationships among the data.

Data mining, however, is a computer intensive and complex tasks. Furthermore, data mining in the social media context requires the mining of very large datasets, which may include millions of records. In such a scenario, it may take hours or even days to build a single model based on such a dataset. Current systems that perform data mining analysis tend to provide inadequate performance for large datasets, and in particular, do not provide scalable performance, as a wide variety of models must be generated to meet specific yet widely different needs.

Currently, there are no tools in existence that utilize these technologies to help automate the process of analyzing talent and determining whether the individual in question can be successful in a respective entertainment field.

As such, a need exists for a system and method to identify quantitative factors in social media postings that can be used to determine the success of a particular individual in the entertainment industry.

SUMMARY OF THE INVENTION

The following summary of the invention is provided in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

To achieve the foregoing and other aspects and in accordance with the purpose of the invention, a system and method for automating a process to evaluate talent is presented.

Accordingly, it is an object of the present invention to provide a new and improved system and method that serves multiple purposes and is convenient and easy to use.

Another object of the present invention is to provide a new and improved system and method automating the talent evaluation process using video and audio found on the world-wide web.

Another object of the present invention is to provide a new and improved system and method for automating the talent evaluation process using online video performances and any features in the data set that correspond to a probability of success attributable to such videos.

Another object of the present invention is to provide a new and improved system and method to predict with a certain degree of accuracy which talent would be more than likely to be a commercial success.

Another object of the present invention is to provide a new and improved system to automatically identify and rank talent using machine learning, such as a random decision forest formed of a plurality of distinct, trained decisions trees. In addition, rather than merely using conventional social-media KPIs (e.g., how many followers does a user have, how many likes does each post receive) as the variables in the decision tree, the decision trees will also use audio and video samples that have been converted into objective quantitative data. Prioritizing the talent in such a manner is important to a talent scouts so they are able to find the individuals who are most likely to succeed in an efficient and effective manner.

Another object of the present invention is to utilize the technological advances made in data mining and RFs to increase the efficiency and effectiveness of the system beyond what is currently possible.

Another object of the present invention is to provide a new and improved system and method that is easy and inexpensive to construct.

In exemplary embodiments, a method in a computing system having a processor and a user interface (UI) for discovering talent, ranking talent, or both is provided. The method describes receiving a plurality of the media at a server, the media being performance based media, transforming the media into at least a data set corresponding to at least a characteristic of the media, identifying features in the data set that correspond to a probability of success, receiving subjective opinion polling data from a plurality of participants as to whether the subject in the media has talent, training a node in a machine learning algorithm to identify, using the performance indicators and the subjective opinion polling data provided whether a being in the subject is likely to have talent, executing the machine learning algorithm to output a ranking of the talent in the media.

In another embodiment, a media selection system for discovering or ranking talent portrayed in the media, the system having computer readable medium comprising a program of machine executable instructions for a programmable computer system that, when executed by the programmable computer system, will cause the programmable computer system to execute instruction, is provided. The system comprises a media pooling module configured to receive a plurality of the media at a server, the media being performance based media; a feature processing module configured to transform the media into at least a data set corresponding to at least a characteristic of the media, a success predictor module configured to identify features in the data set that correspond to a probability of success, receive subjective opinion polling data from a plurality of participants as to whether the subject in the media has talent, a machine learning module configured to train a node in a machine learning algorithm to identify, using the performance indicators and the subjective opinion polling data provided, whether a being in the subject is likely to have talent, a talent prioritization module configured to execute the machine learning algorithm to output a ranking of the talent in the media.

Other features, advantages, and aspects of the present invention will become more apparent and be more readily understood from the following detailed description, which should be read in conjunction with the accompanying drawings.

DETAILED DESCRIPTION OF THE INVENTION

The present invention is best understood by reference to the detailed figures and description set forth herein.

Embodiments of the invention are discussed below regarding the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described are shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

As used herein, the term "features" shall refer to those metrics used to measure the performance of a video posted to the World Wide Web. In one embodiment of the present invention, the features may include statistics such as the number of likes, dislikes, comments, and shares a video posted to a social media network found within the World Wide Web.

As used herein, the term "media" shall refer to video, audio, photographs, and the like.

As used herein, the term "talent" or "subject" shall refer to any individual or group that performs a specific skill (e.g., signs, dances, plays an instrument) with the hopes of performing that skill professionally in the entertainment industry as a career.

As used herein, the term "talent scout" or "talent agent" shall refer to any individual or business that utilizes the system and methods described herein to find talent.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be also understood to refer to functional equivalents of such structures. The present invention will now be described in detail with reference to embodiments thereof as illustrated in the accompanying drawings. While reference is made to cellular phones, the present invention is applicable to other mobile devices such as e-readers, tablets, and the like.

In the descriptions below, a system that ranks and presents data and information is presented in FIGS. 1 and 2, with a method that may be performed utilizing machine learning algorithm (random forest, neural network, etc.) prior to ranking perspective talent based on the predicted success levels is presented in FIG. 3. In connection therewith, the process for training the decision trees for the machine learning algorithm is discussed with reference to FIGS. 4, 5 and 7, and a process for using the trained decision trees for detecting, classifying and ranking the talent is discussed with reference to FIG. 6.

Figure 1:
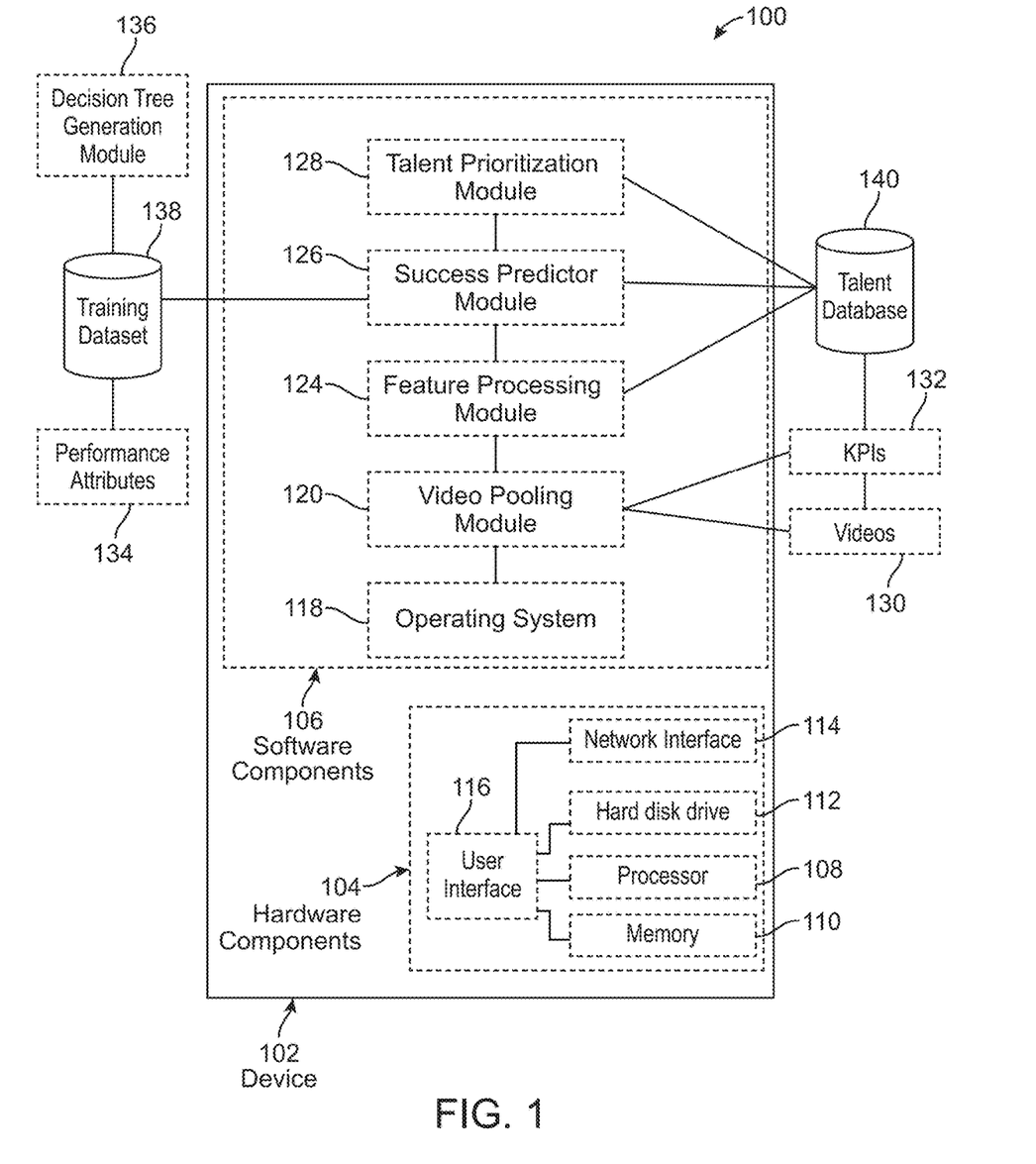
FIG. 1 is a block diagram of an embodiment showing a computer system associated with a system for analyzing, ranking and storing online creative content, in accordance with one embodiment of the present invention.

Referring now to FIG. 1, a diagram of an embodiment of a computer-based system that is configured to gather input data, rank and score talent as an output is shown generally at reference numeral 100. The embodiment 100 is an example of a computer network environment in which a ranking system may operate with various social media networks, the World Wide Web, and consuming applications. The embodiment 100 illustrates the functional components of a system. In some embodiments, the functional components may comprise of a hardware component, a software component, or a combination of hardware and software components. Some of the components may be application level software, while other components may be operating system level components. In some embodiments, the connection of one component to another may be a close connection where two or more components are operating on a single hardware platform. In other embodiments, the connection may be made over network connections spanning long distances. Each embodiment may use different hardware, software, and interconnection architectures to achieve the described functions.

Still referring to FIG. 1, the device 102 comprises a set of hardware components 104 and software components 106. The hardware components 104 may represent an architecture of a computing device, such as a desktop computer or server. In some embodiments, the device 102 may be a personal computer, network appliance, interactive kiosk or other device. The device 102 may also be a portable device, such as a laptop computer, netbook computer, personal digital assistant, mobile telephone, or other mobile device.

Still referring to FIG. 1, in the present embodiment the hardware components 104 may also include a central processing unit 108, random access memory 110, nonvolatile storage 112 and a network interface 114. The random-access memory 110 may store executable code as well as data that may be immediately accessible to the processor 108, while nonvolatile storage 112 may store executable code and data in a persistent stage. The network interface 114 may include hardwired and wireless interfaces through which the device 102 may communicate with other devices. The hardware components 104 may also include one or more user interface devices 116, which may include monitors, displays, keyboards, pointing devices, and any other type of user interface device. The use of the random access memory 110 will be further discussed in relation to FIG. 2.

Still referring to FIG. 1, in an embodiment of the present invention, the software components 106 may include an operating system 118 on which various applications may execute, as well as a media (e.g. videos) pooling module 120 that sources all of the applicable videos 130 and their applicable features 132 for the talent from the World Wide Web and stores them in the talent database 140. As further discussed in connection with FIG. 2, in exemplary embodiments, initially, the talent will be identified by a plurality of talent scouts who will either subjective rank the talent in binary fashion as either good or bad, or a sliding scale, for example from 1-10 or 1-100. In optional embodiments, the talent may be sourced from the World Wide Web based upon a set of subjective talent attributes provided by the talent scout and certain features that establish talent. Other objective measures such as video and audio quality may also be incorporated. Subjective subject matter may be used by the system as well as described herein.

Still referring to FIG. 1, a feature processing module 124 is configured transform the content stored in the talent database 140 into quantitative features that can be analyzed by a machine learning algorithm as part of the success predictor module 126.

Still referring to FIG. 1, a success predictor module 126 computes the probability that the talent presented in the talent database 118 would be a successful entertainer based upon the videos sourced for such talent and may assign a ranking to each one of the potential talents. The success predictor module 126 assigns these rankings by utilizing certain defined performance attributes 134, which includes attributes such as video quality (e.g., good quality video, bad quality video), audio quality (e.g. clear audio, noisy, low quality audio) and the movements in the video (e.g., fluid movements within video, choppy body movements, uncoordinated body movements), as well as the specific KPIs 132 gathered for each of the corresponding videos 130, all of which is saved within the training dataset 138 and then processed using the machine learning module to generate, in some embodiments, a decision tree is generated to determine the ranking. In optional embodiments, other machine learning techniques. In operation, the machine learning module 136 will generate the forest of decision trees used in the Random Forest algorithm (RFA) based on the training dataset 138, but other machine learning processes may be used. Furthermore, historical talent data for generating and training the decision trees (i.e., the "training dataset") may also be stored in the training dataset 138. Once the success predictor module 126 analyzes the corresponding videos for each talent presented, the talent prioritization module 128 will rank and present the talent in the talent database 140 in order from likelihood of most successful to least successful. This is further discussed in relation to FIGS. 5-7.

As mentioned above, the success predictor module 126 may use any machine learning technique, neural network or ensemble learning methods such as random forest for classification and regression in which a multitude of decision trees at training time and outputting the class that is the mode of the classes (classification) or mean prediction (regression) are used to build an ensemble (or "forest") of decision trees that are used to prioritize the talent in the talent prioritization module 130. In embodiments, random forest is used. The RFA is a non-parametric ensemble approach to machine learning that uses bagging to combine decisions of multiple classification (or decision) trees to classify data samples, in this case the videos for each of talent to determine if they will be successful entertainers or not. More details about the RFA may be found in L. Breiman, "Random Forests," Machine Learning 45 (1):5-32 (2001) and A. Liaw et al., "Classification and Regression by Random Forest," R News, Vol. 2/3, p. 18 (2002), both of which are incorporated by reference. Generally speaking, machine learning comprises an intake of mining of data for training one or more learning algorithms.

Figure 3:
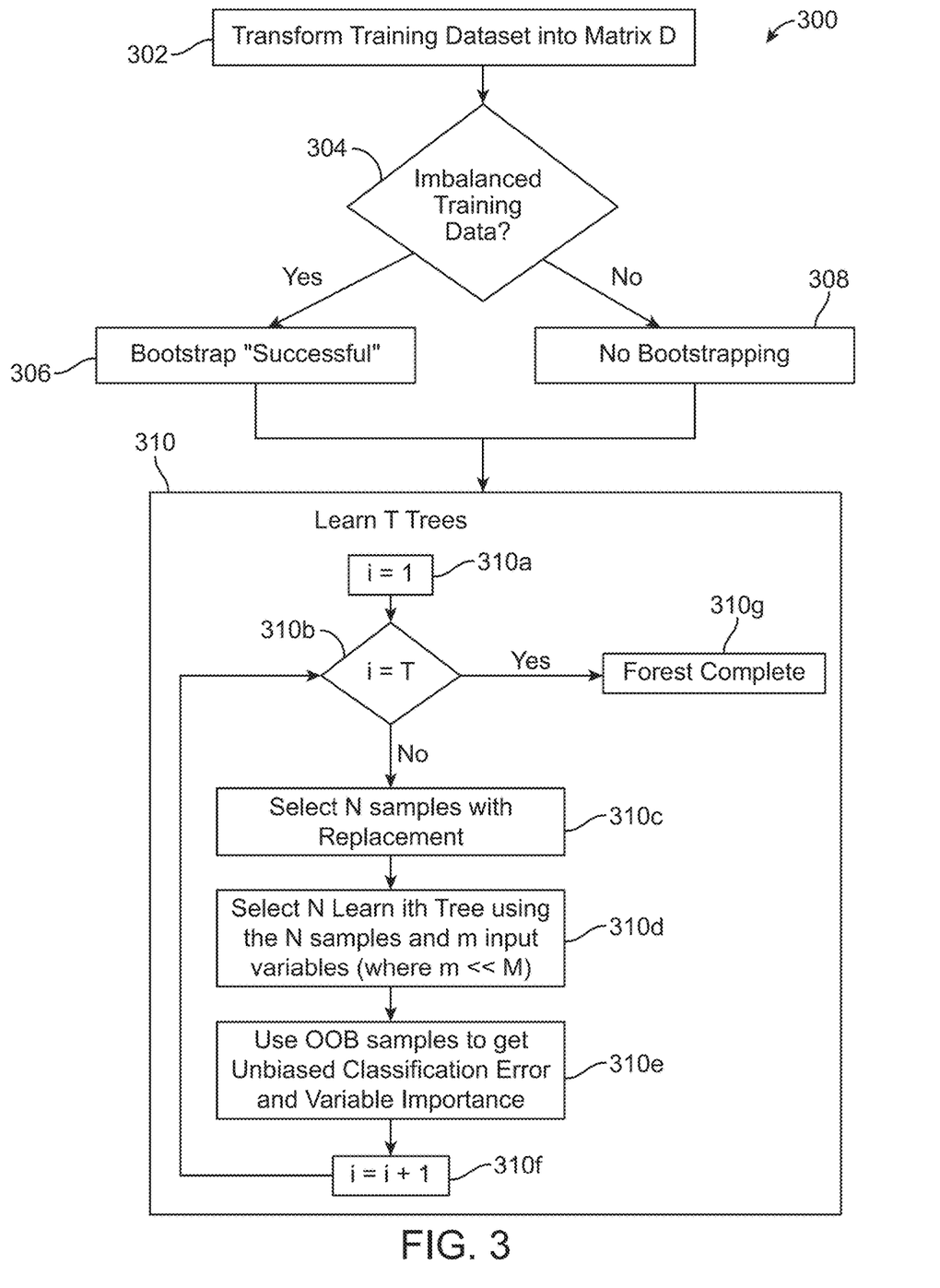
FIG. 3 illustrates a schematic diagram of an exemplary portion of a RF decision tree in accordance with one embodiment of the present invention.
Figure 4:
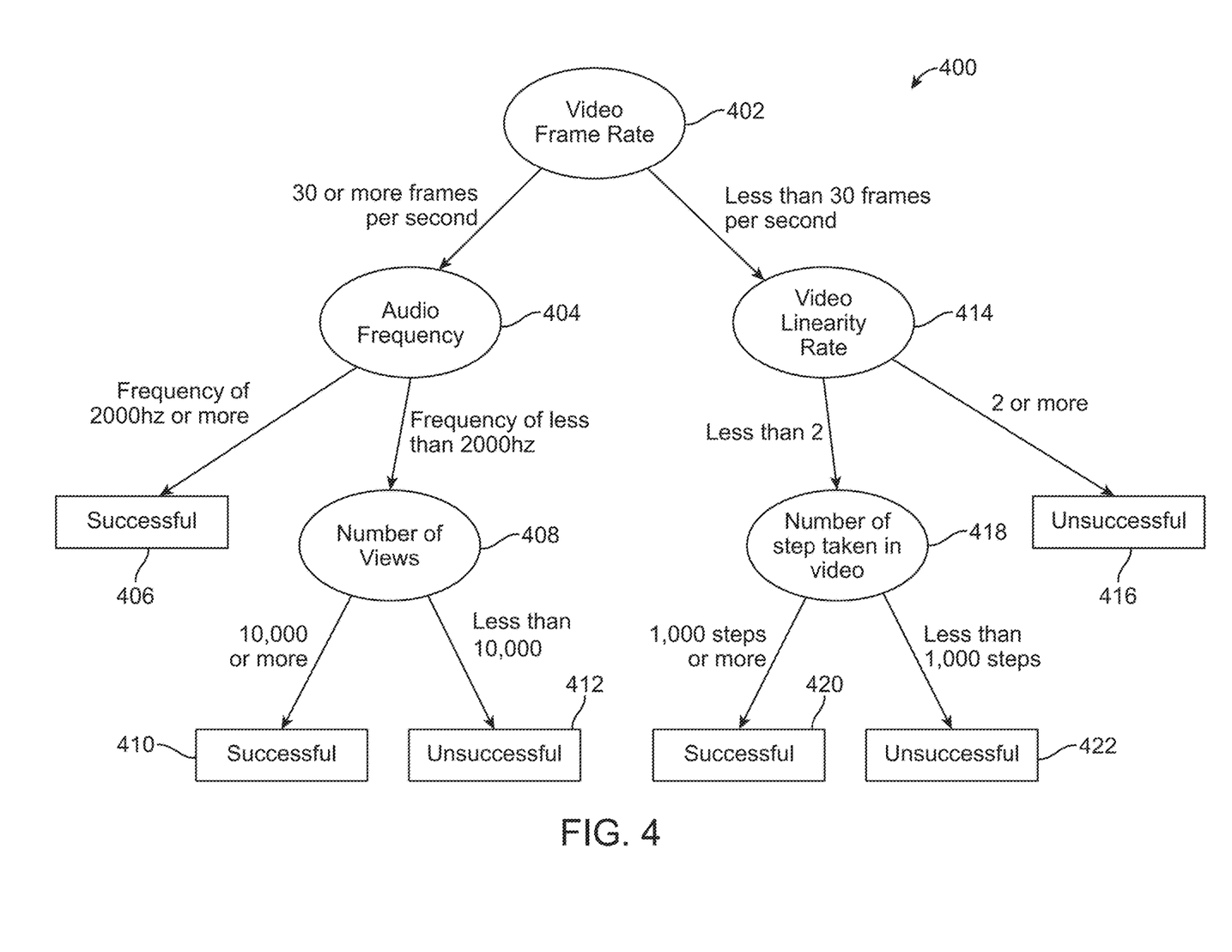
FIG. 4 is a flowchart illustrating the process for training a decision forest to identify features in certain talent performances, in accordance with one embodiment of the present invention.

Initially, training of the forest may occur, which is discussed in greater detail with relation to FIGS. 3 and 4. As an overview, training a node may comprise using previous media and subjectively classifying it as good or bad based on a scout. It may also comprise objectively classifying the media as good or bad based on video quality, or historical measures (e.g., media by famous artists). As more data is input into the algorithm it will train itself based on feedback received based on its initial outputs.

In one embodiment, a talent scout may identify one or more objective datasets based on posted videos and make standard assumptions on the talent's likelihood of being a success in the entertainment industry. The system datamines these datasets, taking into consideration the performance attributes 134 requested by the talent scout 202 to extract a sufficient dataset within a specific category to train one or more learning algorithms. The types of attributes are discussed further herein, but is important to note that they may be purely objective, or combine objectivity and subjectivity. The process through which the machine learning module 136 generates the decision trees is further discussed in accordance with FIG. 3, FIG. 6 and FIG. 7.

The data mining needed to create a strong learning algorithm aims at surfacing and ingesting vast amounts of data from videos posted on the World Wide Web, whether automatically or semi-automatically, and therefore the learning module 136 is configured to analyze large quantities of data to extract patterns such as groups of data records, unusual data (anomaly detection), and dependencies (association rule mining, sequential pattern mining). This may involve using database techniques such as spatial indices. These patterns can then be seen as a kind of summary of the input data, and may be used in further analysis or, for example, in machine learning and predictive analytics.

In this way, based inputs discussed herein, the machine learning module 136 can ingest new videos, compare them to previous videos, and output a prediction as to whether the talent or subject in the new media will be commercially successful, or is talented, generally (the two can be very different). The machine learning module is configured to output a score ranging from 0.0 for little to no chance of success or talent, to a maximum of 1.0 for maximum chance of success or talent based on vectors, as one example. The training data is an important component for the learning module 136 to be able to produce an accuracy score to determine a talent's likelihood of being successful. The algorithm can produce an accuracy score by comparing media, as encoded, to the vector space described by the positive training data related to the maximum level of success and level of success.

In optional embodiments, learning recurrent neural networks may use hidden computational nodes and various gates and may be self-tuning and/or user-tuning. After the process of tuning, the algorithm will be evaluated to assess the degree to which it accurately identifies the talent test data it has never encountered with the "vector space" it has been trained to recognize. This, over time, improves accuracy.

Figure 2:
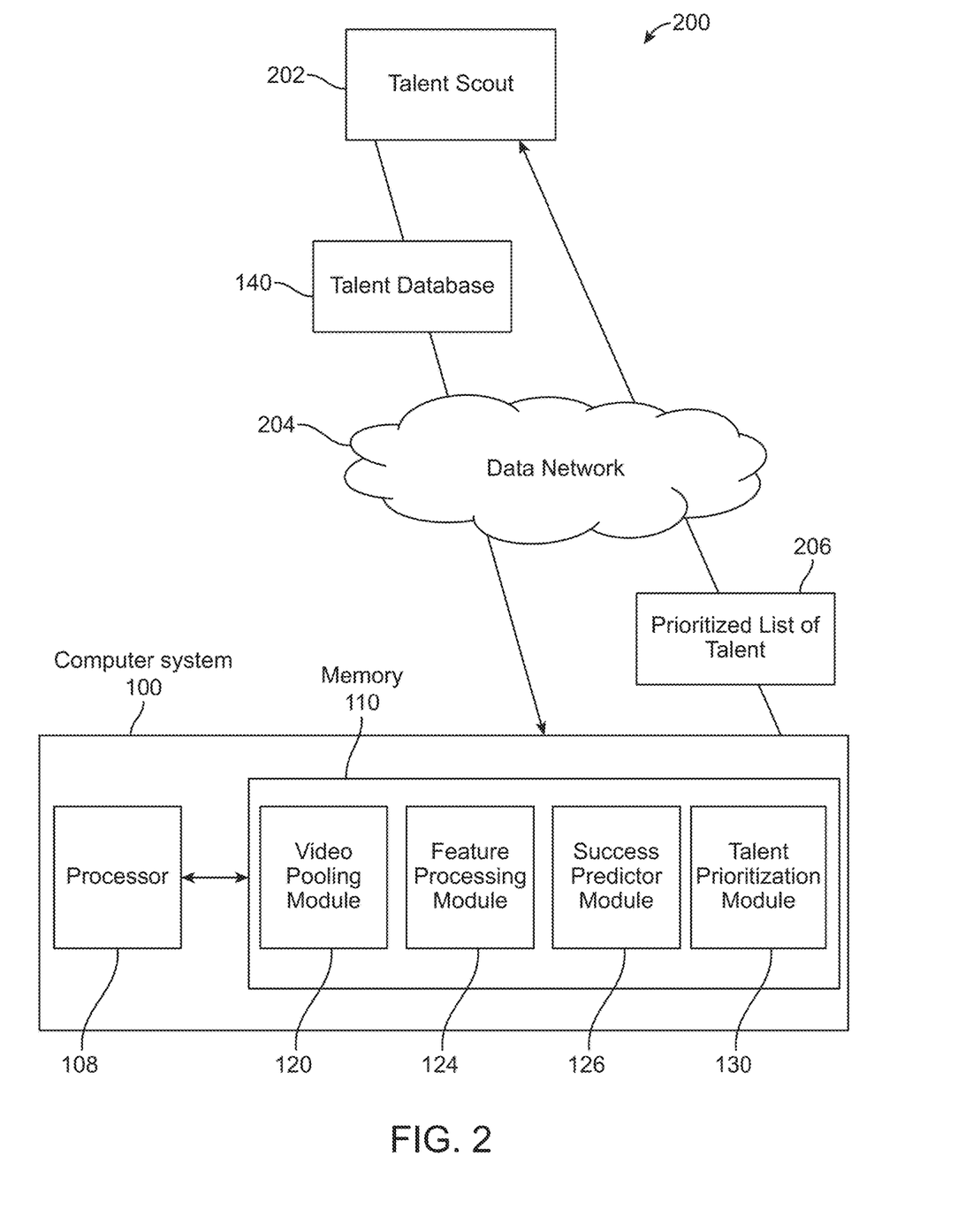
FIG. 2 is a block diagram of a system for ranking talent in accordance with one embodiment of the present invention.

Referring now to FIG. 2, a block diagram of an exemplary system for ranking talent in accordance with one embodiment of the present invention is shown generally at 200. In this diagram, suppose that a talent scout 202 wants to find new talent to represent. To develop the talent database 140, the talent scout 202 may compile a list of the type (pop, rock, R&B) of known talent that it is interested in representing. The talent scout 202 transmits the initial talent database 140, which comprises the initial list of talent, to the computer system 100, which was previously described in accordance with FIG. 1, via a data network 204. The data network 204 may be any suitable data network for transmitting such data files; preferably, this data network 204 would be an IP network such as the Internet, intranet, extranet, etc. It could also use other types of communication protocols, such as Ethernet, and wireless networks. The talent database 140 is then used by video pooling module 120 to gather the videos 130 and corresponding KPIs 132 for each of the talent identified within the talent database 140. This information is then transformed, as may be necessary, into quantitative values through the feature processing module 124 so that it may be read by the success predictor module 126, which uses machine learning/random forest to calculate the talent's likelihood of being a successful entertainer using the videos sourced, and a set of performance attributes about the specific performance embodied in the video. These calculations together with initial subject determinations of scouts are used to then rank the talent in the success predictor module 126. As such, some of the categories of information about the videos may relate to nodes of the decision trees used to calculate the probability of the performance attributes found within each video as being indicative of a successful entertainment career for the talent—these categories may include certain KPIs and other non-conventional data such as:

Reach or distribution potential, such as number of fans and followers, number of times they are mentioned in other posts, their overall reach, blog subscribers, and inbound link clicks;

Engagement and interaction potential, such as likes, comments, social media shares/retweets, forwarding, reviews, check-ins, contributors and active contributors, clicks on your links and page views, unique visitors from social media, sessions from social networking sites and the time spent thereon, average response times;

Quality of video, such as if the quality appears to be professional, properly compressed for web usages, contain crisp scenes, choppy transitions;

Quality of audio, such as professionally mixed and mastered, not improperly compressed, vocal range, high spikes; and Body movements, such as crisp movements and number of steps taken.

Movements in the media can be analyzed by running image recognition on the frames extracted from the video and automatically recognize the real-life objects contained therein. The data on the presence or lack of recognized objects, as well as their estimated share of the video duration, would then become additional features to be used by the model. Audio can also be automatically extracted features such as timbre, mel-frequency cepstral coefficient, root-mean-square energy, spectral centroid, and the like.

Subjective data may also be included based on the rankings by the agents in some embodiments. The computer system 100 then transmits a prioritized list 206 of the talent ranking the probability they will be a successful entertainer back to the talent scout 202 via the data network 204 (or a different data network).

Still referring to FIG. 2, as well as the computer system presented in FIG. 1, the memory 110 may store the software that is executed by the processor 108. In particular, the memory 110 may store the video pooling module 120, the feature processing module 124, the success predictor module 126 and the talent prioritization module 130.

Referring now to FIG. 3, in embodiments in which a decision tree is used (e.g., random forest), a flowchart of a process for generating the forest of decision trees in accordance with one embodiment of the present invention, is shown generally at 300. Firstly, in step 302 the training dataset 138, which may be a based on videos of historically successful talent or be based on a group of scouts ranking "unknown" talent in videos on a binary or sliding scare. The former may be considered "previous media" and the latter may be considered "new media" herein. This data is transformed into actionable numeral values as necessary (if not already done so). This step 302 may include generation of a N×M data matrix, denoted D, where each of the N rows represents one potential talent in the training dataset 138 and each column M represents one input variable used in the classification. In the present embodiment, the input variables are the performance attributes which include the objective KPIs and other non-conventional categories of data such as: the number of fans and followers, number of times they are mentioned in other posts, their overall reach; the number of likes, comments, social media shares/retweets, forwarding, reviews unique visitors from social media; the quality of any video recordings; the quality of an audio recordings; and the movements contained within any video. In particular, performance attributes that have found to be important in the realm of talent evaluation include: the number of fans and followers the talent has; the number of likes and comments the talent's creative content receives, as well as the number of shares; the ability of the talent to reach different vocal notes; and the talent's dancing ability. In optional embodiments, subjective rankings of videos from talent scouts are also used, those videos being compared to other "new" videos for certain qualities that have a determinable effect on success, as described in more detail below.

In the present embodiment, a training dataset encompassing specific performance attributes relating to videos for past talent successfully scouted via the World Wide Web is used. In such cases, historical training data of successful talent that has been discovered on the World Wide Web can be aggregated and used to construct the trees. In optional embodiments, however, a training dataset of performance attributes that a talent scout require in the talent is used. In such cases, the talent scout may provide a list of performance attributes it is specifically looking for and videos only containing those attributes can be used to build the trees. In either case, larger training datasets are generally better and lead to better classifiers, all other things being equal. Also, in either case the number of talent that may be "Successful" may be much smaller than the number of talent deemed "Unsuccessful," which can result in an unsatisfactorily imbalanced dataset. Accordingly, at step 304 the training dataset is examined to see if it is unsatisfactorily imbalanced. That is, for example, if the ratio of successful matches to unsuccessful matches is less than a threshold value (e.g., 1:100), then at step 306 the training dataset can be resampled until it is at an acceptable level (e.g., between 1:10 and 1:50). Conversely, if the ratio of successful matches to unsuccessful matches in the training dataset is acceptable at step 304, no resampling is required as denoted by step 308.

A goal of the trained decision forest is to determine which talent will likely be a successful entertainer based upon certain features and specific performance attributes found in the video performances of each talent, and therefore the machine learning system is trained to identify talent as either successful or unsuccessful. Thus, the successful and unsuccessful examples are generated from Matrix D.

Still referring to FIG. 3, at step 310, a large number, denoted T, of decision trees (e.g., a forest) are generated based on the training dataset 138. The training data set may be, in some embodiments, subjective analysis performed by a plurality of talent scouts, and in other embodiments, objective historical data and media, or a combination of both. As previously discussed, random decision forest is a collection of deterministic decision trees that can be used in classification algorithms, but which also suffer from overfitting and in-turn leads to poor generalization. However, an ensemble of many randomly trained decision trees (a random forest) yields improved generalization. During the training process, the number of trees is fixed. In one embodiment, the number of trees may be 100, although larger values such as 250 or 500 may be used. Each of the trees splits the training dataset 138 into subsets based on an attribute value test, and gives a classification (e.g., "successful" or "unsuccessful", "talented" or "not talented"). When predicting the probability, each input row vector (which corresponds to a subject in the media in the training set) is put down each of the trees in the forest and gets a vote for "Successful" or "Unsuccessful", "talented" or "not talented". The probability of a talent being either successful or unsuccessful depending on the talent scout's requested performance attributes is calculated by taking the number of votes for Successful/Talented for the talent and dividing it by the total number of trees in the forest.

Referring now to FIG. 4, an example of a possible decision tree in accordance with one embodiment of the present invention, in which objective video and audio evidence is used, the tree being shown generally at shown at 400. In this example, the root node 402 is the "Video Frame Rate." We can make an assumption that it is more likely than not that if the video quality is good, e.g., a frame rate of 30 or more frames per second, then it is more likely the person is more talented. Clearly in many instances this will not apply, but this is only one of many factors run through the machine to make the probabilistic determination. Then, the tree branches to the left to the "Audio Frequency" node 404. Here, if the talent's video has an audio frequency of 2000 hz or more, the tree branches to the left to a "Successful" leaf 406. Going back to the "Audio Frequency" node 404, if the talent's video has an audio frequency of less than 2000 hz, the tree branches to the right to the "Number of Views" node 408. Here, if the talent's video has 10,000 or more views, the tree branches to the left to a "Successful" leaf 410. Conversely, if the talent's video has less than 10,000 views, the tree branches to the right to a "Unsuccessful" leaf 412.

Going back to the root node 402, if the talent's video has a frame rate of less than 30 frames per second, the process branches to the right to the "Video Linearity Rate" node 414. Here, in this example, if the talent's video has a linearity rate of 2 or more, then the tree branches right to a "Unsuccessful" leaf 416. However, if the talent's video has a linearity rate that is less than 2, then the tree branches left to the "Number of Steps Taken in Video" node 418. Here, if the talent takes 1,000 or more steps in its video, then the tree branches left to a "Successful" leaf 420. Conversely, if the talent takes less than 1,000 steps in its video, then the tree branches right to a "Unsuccessful" leaf 422. The manner in which the parameters used by each of the split nodes are chosen and how the leaf node probabilities are computed is now described with reference to the remainder of FIG. 3.

Referring back to FIG. 3, as part of step 310, to generate the forest of T decision trees, a counter, denoted i, may be set initially to a value of 1 at step 310a. That counter is then tested to see if it equals T at step 315b to see if the desired number of trees for the forest has been built. If not, more trees need to be generated as the counter has not yet incremented to the value of T. So at step 310c, in various embodiments, the ith decision tree is learned. In this process, according to various embodiments, N sample points (same as the number of talent (rows) in the matrix D) are selected at random with replacement from the training dataset 138 to be treated as the new "training dataset" for the specific tree. "With replacement" means that particular talent samples can be selected multiple times to get to the N sample points, and some of the talent samples are not selected at all. The samples that are not selected can be called the "out-of-bag" (or OOB) samples, and preferably about one-third of the original samples are left out. That is, the percentage of samples selected may be expected to be, or converge to, (1-1/e) or about 63.2%, when the total number of sample points goes to infinity. These OOB samples may be used to obtain an unbiased estimate of the classification error and variable importance for the decision tree, as described further below.

Still referring back to FIG. 3, at step 310d the ith tree is learned. In various embodiments, an optimal number m, much less than M (the number of columns in the matrix D), of variables is decided by the algorithm, such that, at each node in the tree, starting from the top (or root node) and working down, m out of M input variables are selected at random and the best split (according to some criteria) on these m variables is used to split the node. "Best" is usually a measure of homogeneity of the target variables with the subsets, and any suitable technique may be used for determining the best split, such as Gini (population density), entropy, information gain ratio, the Chi-square test, or any other suitable technique.

Next, at step 310e the OOB samples are used to determine the unbiased classification error and variable importance of the ith tree. In various embodiments, the unbiased classification error can be determined by putting each OOB case left out in the construction of the ith tree down the ith tree to get a classification. In this way, a test set classification is obtained for each case in about one-third of the trees. At the end of the run, take j to be the class that got most of the votes every time case n was OOB. The proportion of times that j is not equal to the true class of n averaged over all cases is the OOB error estimate. The OOB error can be used to determine the best split. Also, the OOB can be used to determine the optimal value for m and the total number of trees to construct. The optimal number m and the total number of trees to construct. The optimal number m may be determined by, for example, initially setting it to M divided by 3 (or m=M/3), where M is the total number of columns in the D matrix. When turning m, at each iteration, m is inflated (or deflated) by a predetermined value (e.g., 2), and the iteration stops when the OOB error value does not improve by at least a threshold value (e.g., 0.05). Once m is chosen, m variables are selected randomly and uniformly on each sample to build the trees.

One way to assess the variable importance is with random permutation of the m variables. For example, for every tree grown in the forest, put down the OOB cases and count the number of votes cast for the correct class. The values of variable m can then be randomly permuted in the OOB cases and put the randomly permuted cases down the tree. The number of votes for the correct class in the variable-m-permuted OOB data is subtracted from the number of votes for the correct class in the untouched OOB data. The average of this number over all trees in the forest is the raw importance score for variable m. If the values of this score from tree to tree are independent, then the standard error can be computed by a standard computation, such as dividing the raw score by its standard error to get a z-score, and assign a significance level to the z-score assuming normality. If the number of variables is very large, forests can be run once with all the variables, then run again using only the most important variables from the first run. For each case, consider all the trees for which it is OOB. The percentage of votes or the correct class in the variable-m-permuted OOB data can be subtracted from the percentage of votes for the correct class in the untouched OOB data. This is the local important score for variable m in this case. With the ith tree complete, the counter i is incremented by 1 at step 310*f*, and the process returns t step 310*b*, where the counter i is again compared to T, the desired number of trees. If I does not equal T, the next tree is learned. On the other hand, if i equals T, the next tree is learned. On the other hand, if i equals T, then the forest is complete, shown at step 310*g*, meaning that the desired quantity of trees, T, is constructed. In growing the T trees according to this process, the value of m is preferable held constant to grow the entire forest (that is, each of the T trees is grown with the same value of m) and each decision tree preferably is grown to the largest extent possible without any pruning. In alternative embodiments, the step of determining the unbiased classification error and/or variable important (step 310*e*) may be performed as each tree is generated or it could be performed for each tree after all of the trees are generated (i.e., outside the loop), or combinations thereof (i.e., every x amount of trees). With the forest of decision trees generated, the initial talent database 140 can be prioritized.

Figure 5:
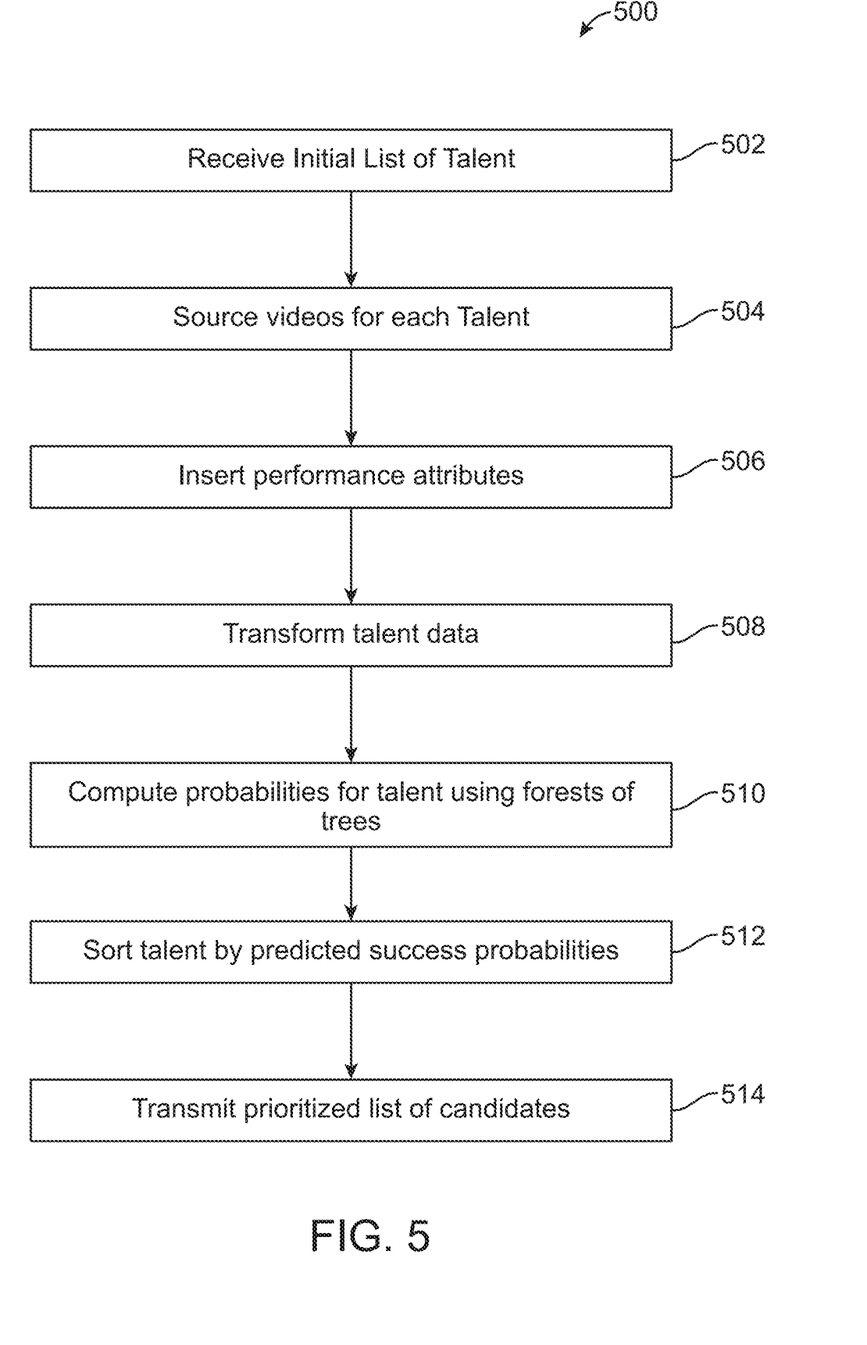
FIG. 5 is a flowchart depicting a process for prioritizing the talent, in accordance with one embodiment of the present invention.

Referring now to FIG. 5, a flowchart of the process that may be performed to prioritize the talent in the talent prioritization module in accordance with one embodiment of the present invention is presented at 500. In this embodiment, a talent scout may ask the operator to locate talent having using specific variables or attributes. At step 502 the computer system receives the initial list of talent or talent attributes from the talent scout, and then at step 504 the computer system sources the videos and associated KPIs for each of talent listed. Next at step 506, the performance attributes are entered into the system.

Still referring to FIG. 5, at step 508 the data for the talent is transformed to a suitable form, preferable a N'×M' matrix, where N' is the number of talent in the initial list and M' is the input variables (primes are used here to differentiate these values from the dimensions of the D matrix used to learn the forest of decision trees).

At step 510 the N'×M' matrix is put down each of the T trees in the forest to determine the probability for each talent. This is done by averaging the outputs of the decision trees for each talent. For example, if a particular talent is classified as Successful for S of the T trees (and conversely, Unsuccessful for T-S trees), that talent's probability is S divided by T (or S/T). Then, at step 512 the talent can be prioritized by sorting them by their predicted success probabilities (computed at step 510) from highest probability to lowest probability. Then at step 514, the prioritized list of talent 208 can be transmitted by the computer system 100 back to the talent scout 202.

As mentioned above, variables other than the KPIs are used in various embodiments to classify and prioritize the talent. These non-KPI variables can include, for example, quality of the videos (e.g., latency issues) and quality of the audio (e.g., audio frequency). Thus, these variables can be associated with nodes for some of the decision trees of the forest.

As should be apparent from the above description, different training datasets will lead to different forests of decision trees. In particular, different variables or attributes will prove more significant in classifying the samples. For example, when a specific training dataset is used that is specific to the talent attributes requested by the talent scout 202, variables that are unique to those attributes are more likely to be used in the trees than if the trees were generated using a general training dataset. Hence, if a talent scout 202 is seeking to find talent that can sing within a certain vocal range, then whether a talent reaches a certain frequency in the video will be a node in the decision trees as opposed to if a general training data is used independent of the specific attributes of the talent scout 202.

As another example, if a talent scout 202 is seeking to find talent who produces only high-quality videos, and this condition is factored into the training, the number of frames per second in the videos may prove to be an important factor (node) in classifying the talent. Prioritizing talent in the manner described above is very important to the talent scout 202. Many times, talent scouts 202 tend to miss out on potential talent because of an inability to watch a video provided to them. Other times, talent scouts 202 are simply unable to find the time to view the many videos sent their way. However, prioritizing talent based on their video performances and their respective KPIs and the performance attributes of the talent scout allows the talent scout to focus only on that talent who will have the highest likelihood of being successful.

Figure 6A:
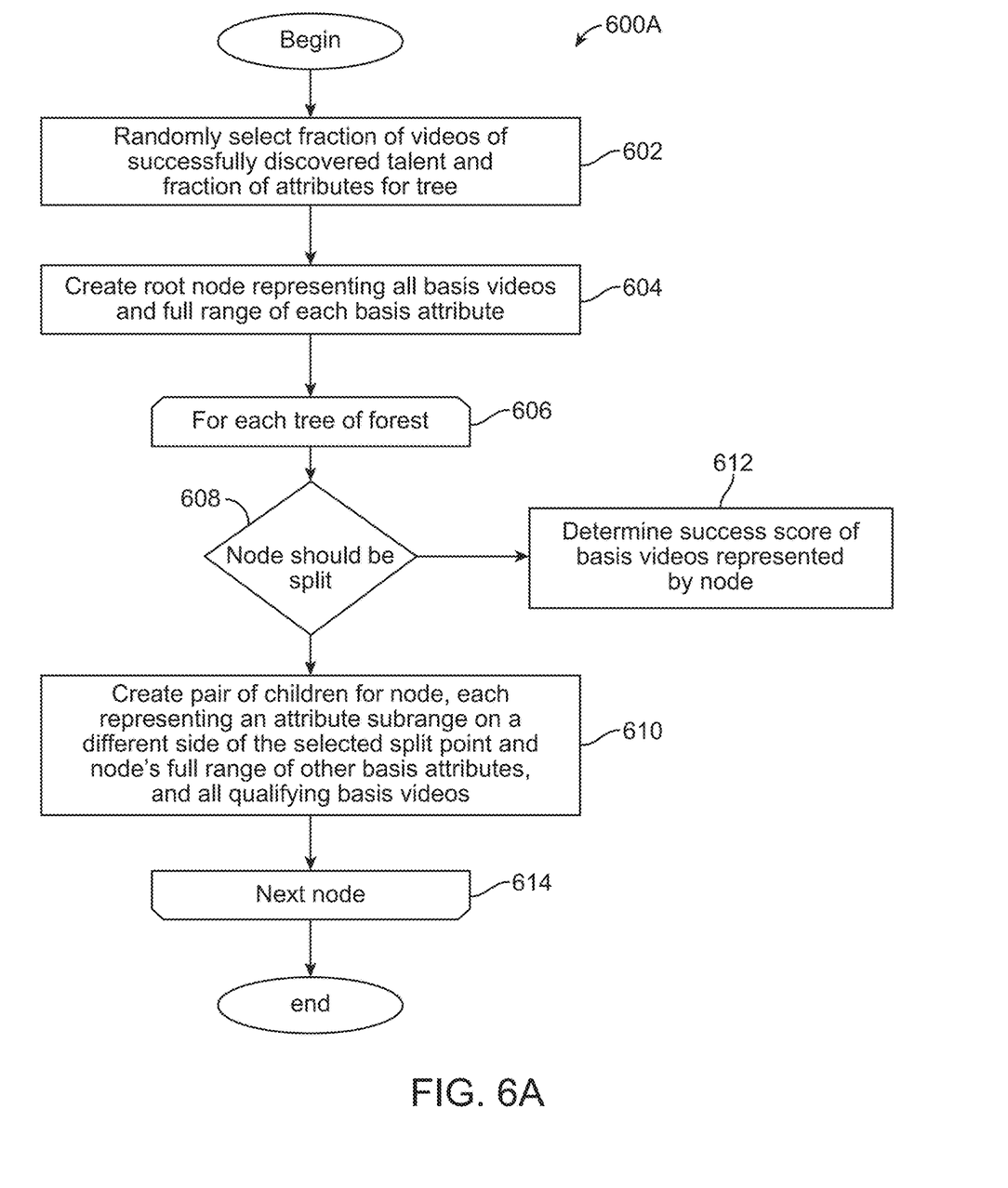
FIG. 6A is a flow diagram showing exemplary steps performed by the facility in order to construct a tree, in accordance with one embodiment of the present invention.

Referring now to FIG. 6A, a flow diagram showing steps typically performed by the system in order to construct a tree in accordance with one embodiment of the present invention, is presented at 600. In step 602, the system randomly selects a fraction of the videos of successfully discovered talent to which the tree corresponds, as well as a fraction of the available performance attributes, as a basis for the tree. These are considered "previous media". In step 604, the system creates a root node for the tree that represents all of the basis videos and the full range of each of the basis performance attributes. In steps 606-614, the system loops through each node of the tree, including both the root node created in step 604 and any additional nodes added to the tree in step 610. In step 608, if it is possible to "split" the node, i.e., create two children of the node each representing a different subrange of an attribute value range represented by the node, then the system continues in step 610, else the system continues in step 612. The way a system determines whether and how to split a node is now discussed with reference to FIG. 6B.

Figure 6B:
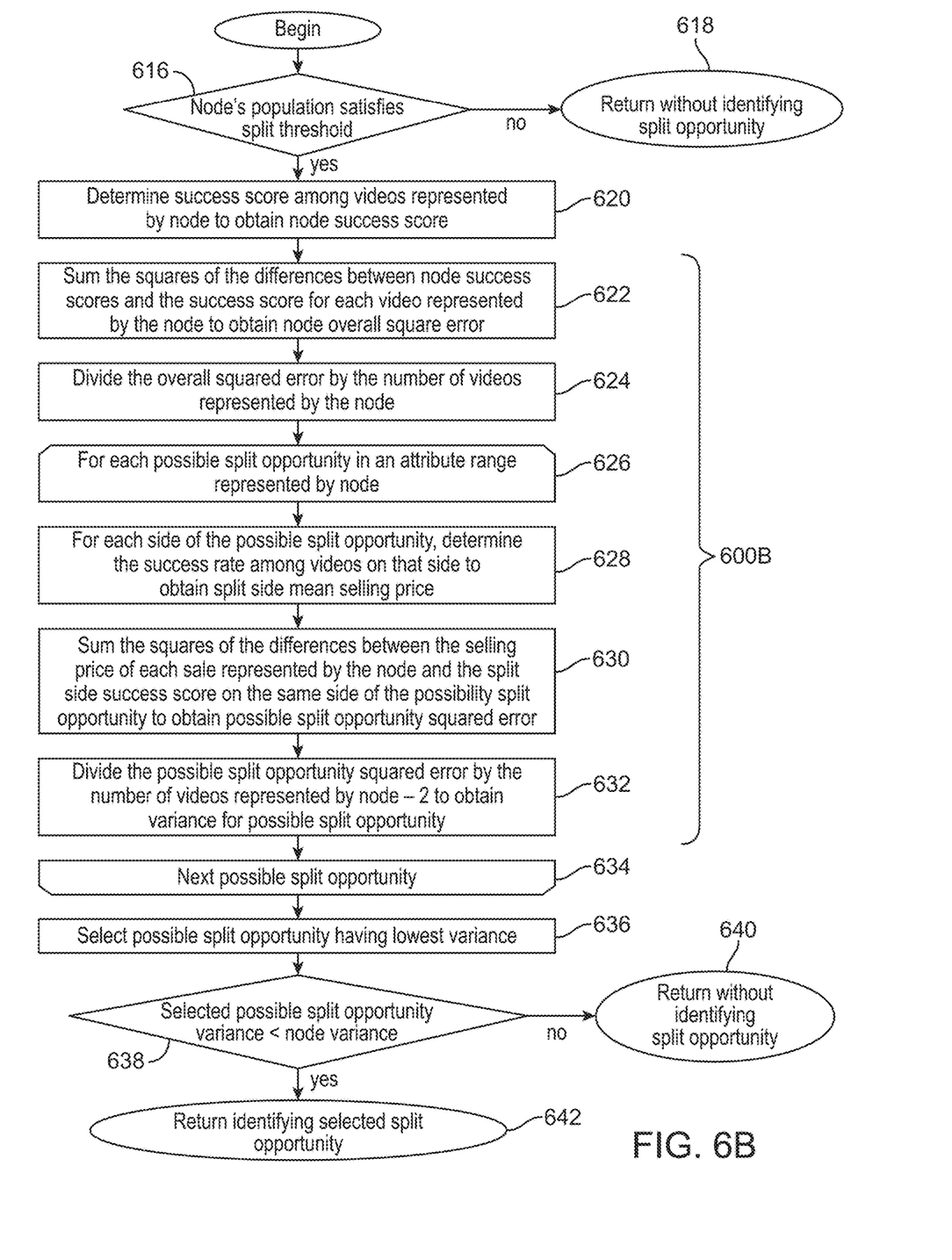
FIG. 6B is a flow diagram showing exemplary steps performed by the system in order to determine whether and how to split a node of a tree, in accordance with one embodiment of the present invention.

Referring now to FIG. 6B, a flow diagram showing steps typically performed by the system in order to determine whether and how to split a node of a tree in accordance with one embodiment of the present invention, is shown at 600B. These steps generally identify a potential split opportunity having the highest information gain, and determine whether the information gain of that potential split opportunity exceeds the information gain of the current node. In step 616, the system determines whether the node's population— that is, the number of basis videos represented by the node—satisfies a split threshold, such as a split that requires more than three basis videos. If the threshold is not satisfied, then the system returns to step 608 in step 618 without identifying any split opportunity, such that the facility will not split the node; otherwise, the facility continues in step 620. Though not shown, the system may apply a variety of other tests to determine whether the node should be split, including whether any of the selected attribute ranges represented by the node is divisible. For example, where the selected attributes are vocal range and video quality, a node represents the ranges vocal range=5 and video quality=no, none of the node's selected attribute ranges can be split.

Still referring to FIG. 6B, in steps 620-624, the system analyzes the characteristics of the node in order to be able to compare them to characteristics of pairs of possible child nodes that would result from different opportunities for splitting the node. In step 620, the system determines the success probability among the videos represented by the node to obtain a node success score for the node. In step 622, the system sums the squares of the differences between the node success score determined in step 622 and the success score of each video represented by the node to obtain a node overall squared error. In step 624, the system divides the overall squared error by one fewer than the number of videos represented by the node in order to obtain a node variance.

Still referring to FIG. 600B, in steps 628-636, the system analyzes the characteristic of each possible split opportunity that exists in the node; that is, for each attribute range represented by the node, any point at which that range could be divide. In step 630, for each side of the possible split opportunity, the system determines the success score among videos on that side to obtain a split side success score. In step 632, the system sums the squares of the differences between the success score of each video represented by the node and split the side mean success score on the same side of the possible split opportunity to obtain a possible split opportunity squared. In step 634, the system divides the possible split opportunity squared error by two less than the number of videos represented by the node to obtain a variance for the possible split opportunity. In step 636, if another possible split opportunity remains to be processed, then the facility continues in step 628 to process the next possible split opportunity, else the system continues to step 638.

Still referring to FIG. 6B, in step 638 the system selects the possible split opportunity having the lowest variance. In step 640, if the selected possible split opportunity variance determined in step 638 is less than the node variance determined in step 624, then the system continues in step 640, else the system continues in step 642 to return, identifying the split opportunity selected in step 638 to return without identifying a split opportunity.

Returning to FIG. 600A, in step 610, when the steps shown in FIG. 600B determine that the node should be split, the system creates a pair of children for the node. Each child represents one of the subranges of the split opportunity identified in step 608 and the node's full range of unselected attributes. Each child represents all basis videos whose attributes satisfy the attribute ranges represented by the child. In step 612, because the node will be a leaf node, the system determines the success score of basis videos represented by the node. In step 614, the system processes the next node of the tree. After step 614, these steps concluded.

Figure 7:
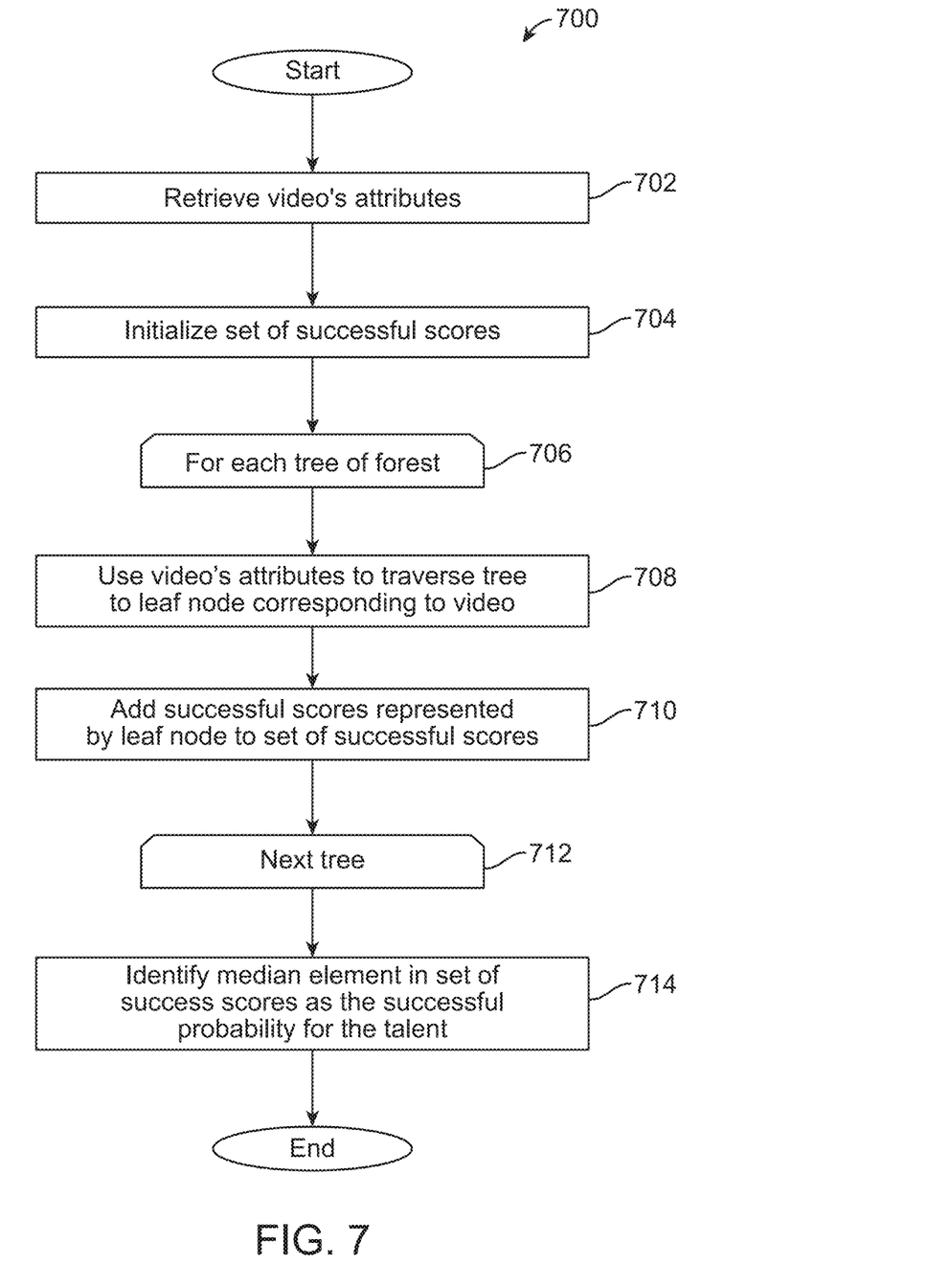
FIG. 7 shows is the steps typically performed by the system in order to apply a forest of decision trees to obtain a ranking for a specific talent, in accordance with one embodiment of the present invention.

Referring now to FIG. 7, a flow diagram showing the steps typically performed by the system in order to apply a forest of trees to obtain a success score for a talent's video in accordance with one embodiment of the present invention, is shown at 700. In step 702, the system retrieves the attributes for a particular talent's videos. In step 704, the system initializes a set of success attributes. In steps 706-712, the system loops through each tree of the forest. In step 708, the system uses the video's attributes retrieved in step 702 to traverse the tree to a leaf corresponding to the video and its attributes. In step 710, the system copies from the leaf node traversed-to in step 708, the list of the success attributes of basis videos represented by the leaf node. In step 712, if additional trees of the forest remain to be processed, then the system continues in step 706 to process the next tree, else the system in step 714. In step 714, the system identifies as its success probability for the talent a median element in the set of success scores accumulated in step 710

Specific configurations and arrangements of the invention, discussed above with reference to the accompanying drawing, are for illustrative purposes only. Other configurations and arrangements that are within the purview of a skilled artisan can be made, used, or sold without departing from the spirit and scope of the invention. For example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures.

While the present invention has been described in connection with what are presently considered to be the most practical and preferred embodiments, it is to be understood that the present invention is not limited to these herein disclosed embodiments. Rather, the present invention is intended for various modifications and equivalent arrangements included within the spirit and scope of the appended claims.

Although specific features of various embodiments of the invention may be shown in some drawings and not in others, this is for convenience only. In accordance with the principles of the invention, the feature(s) of one drawing may be combined with any or all of the features in any of the other drawings. The words "including," "comprising," "having," and "with" as used herein are to be interpreted broadly and comprehensively, and are not limited to any physical interconnection. Moreover, any embodiments disclosed herein are not to be interpreted as the only possible embodiments. Rather, modifications and other embodiments are intended to be included within the scope of the appended claims.

We claim:

1. A method for analyzing media to evaluate talent of a subject portrayed in the media, the method implemented by a non-transitory computer-readable storage medium encoded with instructions that, when loaded into a computer, establish a machine performing a computer-implemented method, the method comprising:

receiving a plurality of the media at a server, the media being performance based media;

transforming, via the server, the media into at least a data set corresponding to at least a characteristic of the media at the server, wherein the server is in communication with a node;

wherein the at least one data set comprise:

a first quantitative data set that directly corresponds video quality;

a second quantitative data set that directly corresponds to audio quality; and a third data set that directly corresponds to subject body movement;

identifying features in the data set that correspond to a probability of success of the subject in the media;

receiving subjective opinion polling data from a plurality of participants as to whether the subject in the media has talent;

training the node via machine learning algorithm to identify, using the identified features in the data set and the subjective opinion polling data provided, whether the subject is likely to have talent;

executing the machine learning algorithm to output a score relating to the talent of the subject in the media using a combination of the first, second and third quantitative date sets and the subjective opinion polling.

2. The method of claim 1, wherein the machine learning algorithm comprises random forest, and the method further comprises:

constructing a training data set from the features, subjective polling data, or both based on media;

analyzing the training data set input into the server;

generating a forest of decision trees based on the training data set;

inputting new media into the server, the new media being the media to be ranked;

prioritizing the media from the subject that most likely to have talent to least likely to have talent.

3. The method of claim 2, wherein training the node generating a forest of decision trees further comprises:

inputting previous media for subjects that are known to be talented based upon commercial success;

inputting subjective opinion polling on the previous media on a binary ranking or a sliding scale ranking from a scout;

generating vector spaces that correspond the inputs;

running the new media through the random forest;

comparing the new media to the previous media, and grouping the new media in the vector space that relates to a probabilistic level of success the subject may have bagging the new media that comprises the new media ranking and continuously running additional media through the node to increase efficacy;

generating the score ranging from 0.0 to 1.0 for the subject in the media.

4. The method of claim 2, wherein generating a forest of decision trees comprises generating an ensemble of a plurality of randomly trained decision trees, wherein each of the decision trees are split into subsets based on an attribute value test, and each of the subjects in the media are given a classification of talented or untalented.

5. The method of claim 1, wherein the subjective opinion polling comprises receiving a binary ranking from a scout or a sliding scale ranking from the scout.

6. The method of claim 1, further comprising comparing the quantitative data sets with a predetermined range of data gathered from the machine learning algorithm to assess the talent of the subject.

7. The method of claim 1, wherein establishing the features comprises reviewing a platform the media resides on to retrieve at least one of the following:

number of followers;

number of times mentioned in posts; and inbound link clicks;

social media comments; and social media shares; and comparing the features to predetermined values to assess the talent of the subject.

8. The method of claim 1, wherein the at least one node is a plurality of nodes that are self-tuning.

9. The method of claim 1, further comprising inputting the features based on a request from a customer into the server, and running the machine learning to output a priority list of media that corresponds to the customer requested features.

10. A system for discovering or ranking talent portrayed in a media, the system having non-transitory computer-readable medium comprising a program of machine executable instructions for a programmable computer system that, when executed by the programmable computer system, will cause the programmable computer system to execute instruction, the system comprising:

a media pooling module configured to receive a plurality of the media at a server, the media being performance based media;

a feature processing module configured to transform, via the server, the media into at least a data set corresponding to at least a characteristic of the media;

wherein the at least one data set comprise:

a first quantitative data set that directly corresponds video quality;

a second quantitative data set that directly corresponds to audio quality; and a third data set that directly corresponds to subject body movement;

a success predictor module configured to:

identify features in the data set that correspond to a probability of success;

receive subjective opinion polling data from a plurality of participants as to whether the subject in the media has talent;

a machine learning module configured to train a node using a machine learning algorithm to identify, using the data set and the subjective opinion polling data provided, whether a being in the subject is likely to have talent;

a talent prioritization module configured to execute the machine learning algorithm to output a score in the talent in the media;

executing the machine learning algorithm to output a score relating to the talent of the subject in the media using a combination of the first, second and third quantitative date sets and the subjective opinion polling.

11. The system of claim 10, wherein the machine learning algorithm comprises random forest, and the machine learning module is further configured to:

construct a training data set from the features, subjective polling data, or both;

analyze the training data set input into the system using a server;

generate a forest of decision trees based on the training data set;

input new media into the system, the new media being the media to be ranked;

prioritize the media from most likely to have talent to least likely to have talent.

12. The system of claim 11, wherein the machine learning module is further configured to:

input previous media for subjects that are known to be talented based on commercial success;

input subjective opinion polling on the previous media on a binary ranking or a sliding scale ranking from a scout;

generate vector spaces that correspond the inputs;

run the new media through the random forest;

compare the new media to the previous media, and grouping the new media in the vector space that relates to a probabilistic level of success the subject may have bag the new media that comprises the new media ranked as good and those ranked as bad, and continuously running additional media through the node to increase efficacy;

generate a score ranging from 0.0 to 1.0 based on the subject in the media.

13. The system of claim 11, wherein generating a forest of decision trees comprises generating an ensemble of a plurality of randomly trained decision trees, wherein each of the decision trees are split into subsets based on an attribute value test, and each of the subjects in the media are given a classification of talented or untalented.

14. The system of claim 10, wherein the subjective opinion polling comprises receiving a binary ranking from a scout or a sliding scale ranking from the scout.

15. The system of claim 10, wherein the talent predictor module is further configured to compare the quantitative data sets with a predetermined range of data gathered from the machine learning algorithm to assess the talent of the subject.

16. The system of claim 10, wherein establishing the features comprises reviewing a platform the media resides on to retrieve the:
- number of followers;
- number of times mentioned posts;
- inbound link clicks;
- social media comments;
- social media shares; and
- comparing the features to predetermined values to assess the talent of the subject.

17. The system of claim 10, wherein the at least one nodes is a plurality of nodes that are self-tuning.

18. The system of claim 10, further comprising inputting on graphical user interface the features based on a request from a customer; and running the machine learning algorithm to output a priority list of media that corresponds to the customer requested features.

\* \* \* \* \*